United States Patent

Whittier et al.

[11] Patent Number: 5,702,080
[45] Date of Patent: Dec. 30, 1997

[54] COMBINATION END CAP AND CLIP FOR BIOPSY FORCEPS INSTRUMENT

[75] Inventors: John R. Whittier, Miami; Sylvestre Cordoba, Miami Springs, both of Fla.; Bruce H. Diamond, Brookline, Mass.

[73] Assignee: Symbiosis Corporation, Miami, Fla.

[21] Appl. No.: 375,402

[22] Filed: Jan. 18, 1995

[51] Int. Cl.$^6$ ............................................ F16B 47/00
[52] U.S. Cl. .................... 248/205.5; 248/683; 248/689
[58] Field of Search .......................... 248/205.5, 682, 248/683, 689, 309.1, 316.7, 316.1, 314

[56] References Cited

U.S. PATENT DOCUMENTS

| | | | |
|---|---|---|---|
| 1,868,023 | 7/1932 | North | 248/205.5 X |
| 1,984,610 | 12/1934 | Warren | 248/683 X |
| 2,006,843 | 7/1935 | Russell | 248/205.5 |
| 2,009,360 | 7/1935 | Koch | 248/205.5 X |
| 2,919,096 | 12/1959 | Cohen | 248/309.1 |
| 3,796,405 | 3/1974 | Rystad | 248/316.7 X |
| 5,078,695 | 1/1992 | Farrar, Jr. et al. | 604/192 |
| 5,171,224 | 12/1992 | Tucker | 604/110 |
| 5,183,469 | 2/1993 | Capaccio | 604/192 |
| 5,334,151 | 8/1994 | Santilli | 604/192 |
| 5,344,011 | 9/1994 | DiBernardo et al. | 206/364 |
| 5,366,444 | 11/1994 | Martin | 604/159 |

Primary Examiner—Ramon O. Ramirez
Assistant Examiner—Stephen S. Wentsler
Attorney, Agent, or Firm—David P. Gordon

[57] ABSTRACT

An end cap is provided for an endoscopic biopsy forceps instrument having a long coil and a jaw assembly. The end cap is provided with a cup portion, an attachment clip, and preferably a suction cup. The cup portion fits over the closed jaws of the biopsy forceps and has an open end and a closed end, and side walls. The attachment clip extends perpendicularly from the side walls of the cup portion and fits around one or more sections of the biopsy forceps coil, thereby stabilizing the forceps jaw and coil for packaging. The attachment clip can also be used for attaching the cap to the coil of the biopsy forceps instrument when the cap is off of the jaws so that the cap is readily available for later retrieval. The suction cup is coupled to the top of the cup portion and is used both to prevent misplacement and loss of the cap, and to expedite recapping after usage.

20 Claims, 3 Drawing Sheets

5,702,080

1

COMBINATION END CAP AND CLIP FOR BIOPSY FORCEPS INSTRUMENT

BACKGROUND OF THE INVENTION

1. Field of the Invention

The present invention relates to endoscopic biopsy forceps devices. More particularly, the present invention relates to end caps for the jaws of a biopsy forceps instrument.

2. State of the Art

Endoscopic biopsy forceps are used for taking tissue samples from the human body for analysis. These forceps typically have a pair of cupped jaws attached to the distal end of a long flexible coil, the proximal end of which is attached to actuating means which opens and closes the jaws when the actuating means is manipulated by the practitioner. The endoscopic biopsy procedure is accomplished through an endoscope which is inserted into a body and guided by manipulation to the biopsy site. The endoscope typically includes a long narrow flexible tube carrying distal optical means and having a narrow lumen for receiving the biopsy forceps. The practitioner guides the endoscope to the biopsy site using the optical means and inserts the forceps, with jaws closed, through the lumen of the endoscope to the biopsy site. While viewing the biopsy site through the optical means of the endoscope, the practitioner opens the forceps jaws and carefully guides the jaws around a tissue to be sampled. When the jaws are in the correct position, the practitioner manipulates the actuating means and closes the jaws on the tissue to be sampled. The cupped jaws grip the tissue and enclose a sample of the tissue in the space between the cupped jaws. The forceps are then withdrawn from the lumen of the endoscope while the jaws are kept shut, with the sample captured in the space between the cupped jaws typically torn away from the tissue at the biopsy site.

Co-owned U.S. Pat. No. 5,228,451 to Bales et al., the complete disclosure of which is hereby incorporated by reference herein, discloses endoscopic biopsy forceps having a long flexible coil with a pair of opposed jaws at its distal end and a handle assembly at its proximal end. Prior to packaging, the jaws of the biopsy forceps instrument are capped with a small resilient plastic cap, which holds the jaws in the closed position and protects them from damage. The biopsy forceps coil is then wound in a loop fashion to minimize space occupancy. The distal end of the coil is typically looped through the coil loops for added stability. The coiled instrument with the capped jaws is then packaged and sterilized. Packaging, however, is awkward and difficult as the distal end of the coil often comes loose, or protrudes out from the wound loops of the biopsy forceps instrument.

SUMMARY OF THE INVENTION

It is therefore an object of the invention to provide an end cap for an endoscopic biopsy forceps instrument which provides for easy and effective packaging and storing of the instrument.

It is also an object of the invention to provide a combination end cap for an endoscopic biopsy forceps instrument which protects the biopsy forceps jaws and holds the coils of the instrument in a looped position prior to use.

It is a further object of the invention to provide an end cap for an endoscopic biopsy forceps instrument which is easily found after it is removed from the jaws of the biopsy forceps instrument.

In accord with the objects of the invention, an end cap for an endoscopic biopsy forceps instrument is provided and

2 generally includes a cup portion and a clip portion. The cup portion of the end cap, which is hollow, includes an open end, a closed end and side walls, and is dimensioned to receive and hold closed the jaw assembly of the biopsy forceps. The clip portion of the end cap extends from the side walls of the cup portion and is dimensioned for fitting around one or more sections of the flexible coil of the biopsy forceps. The clip portion is used for attaching the jaws of the biopsy forceps instrument to the coil of the biopsy forceps instrument for packaging and storage. Thus, when the coil of the biopsy forceps is stored by winding it in a circular-like fashion so as to form multiple adjacent coil loops, the combination end cap is placed over the closed jaw assembly and the clip portion of the end cup is affixed to one or more of the adjacent coil loops so as to stabilize the coil assembly of the biopsy forceps. The clip can also be used after unpackaging to affix the cap to a base section of the biopsy forceps coil for subsequent retrieval.

According to another aspect of the invention, the combination end cap of the invention is provided with a suction cup which is coupled to the top of the closed end of the cup portion for attachment to any smooth surface. By affixing the suction cup to a known location, it can later be easily retrieved for reuse.

Additional objects and advantages of the invention will become apparent to those skilled in the art upon reference to the detailed description taken in conjunction with the provided figures.

DETAILED DESCRIPTION OF THE PREFERRED EMBODIMENT

Figure 1:
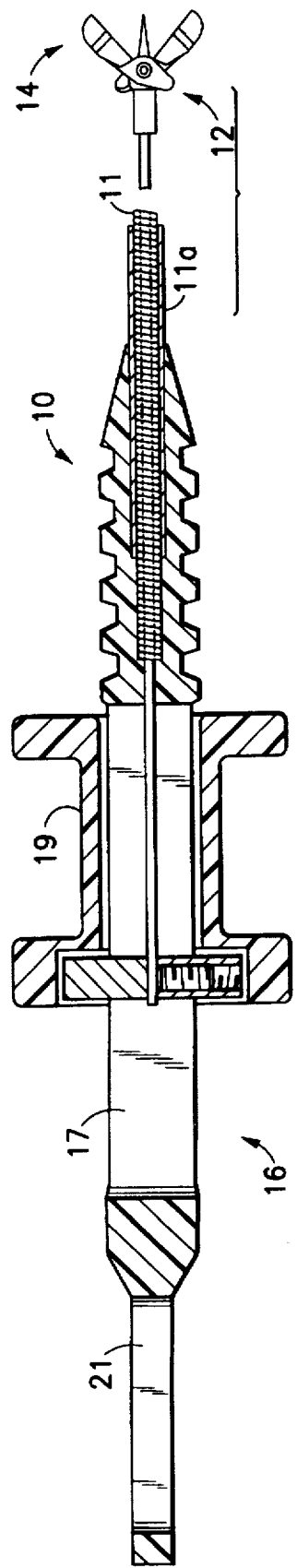
FIG. 1 is a side elevational view in section of a prior art biopsy forceps instrument.
Figure 2:
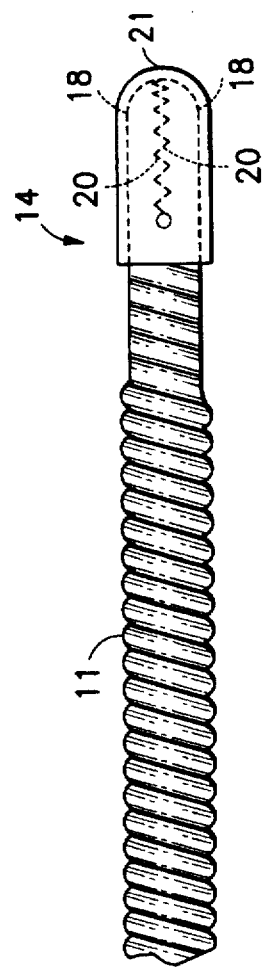
FIG. 2 is a side elevational view partly in section of the prior art end cap in combination with the distal end and jaws of the prior art biopsy forceps instrument of FIG. 1.

Referring now to prior art FIGS. 1 and 2, there is shown a biopsy forceps instrument 10 such as is described in co-owned U.S. Pat. No. 5,228,451 to Bales et al. The biopsy forceps instrument 10 has a distal end 12 with a jaw assembly 14, and a proximal end 16 having a handle 17, spool 19 and thumb ring 21 for manipulation of the jaw assembly 14. The jaw assembly 14 comprises a pair of jaws 18, each preferably having an array of teeth 20 radially directed about the jaws 18. A cap 21 known in the art is fitted over the closed jaw assembly 14 as shown in FIG. 2.

Figure 3:
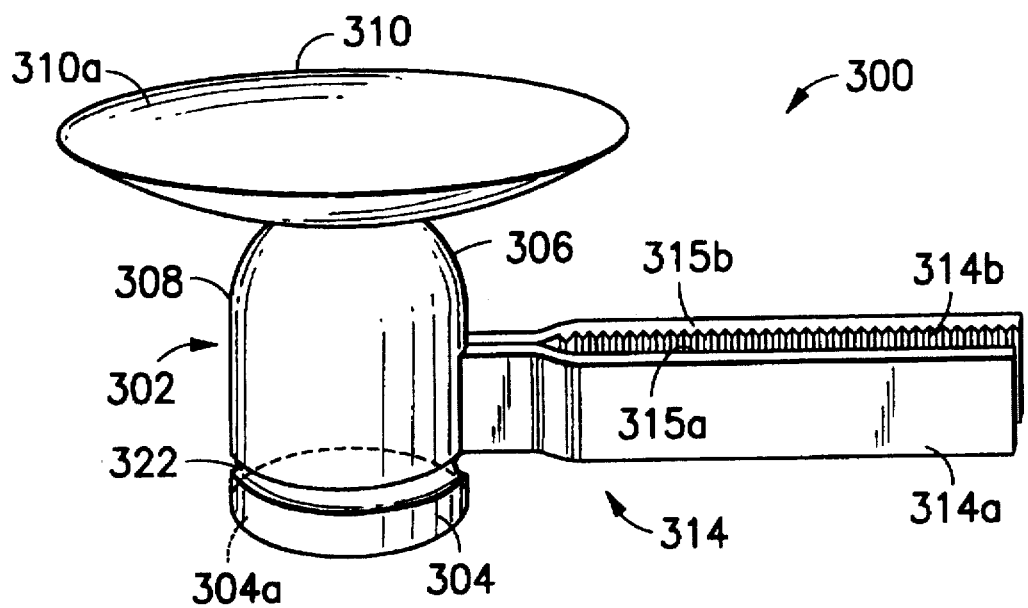
FIG. 3 is a perspective view of the combination end cap of the invention.
Figure 4:
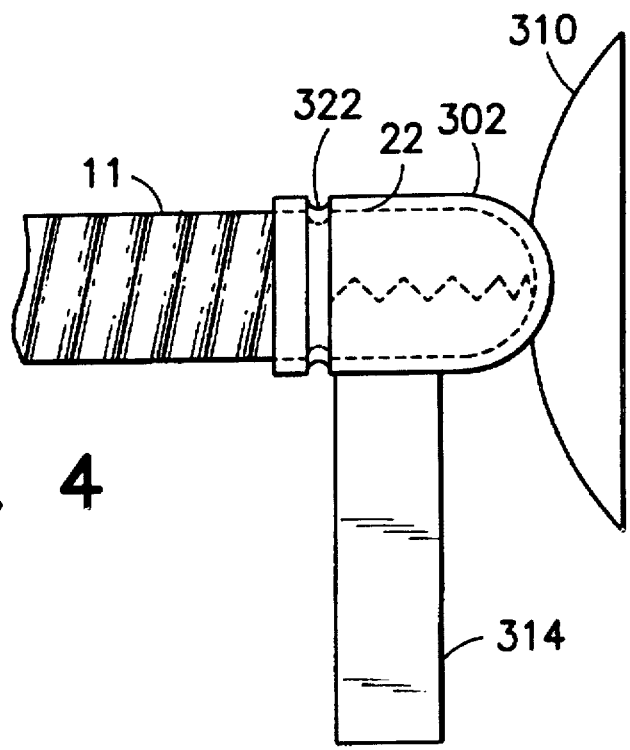
FIG. 4 is a side elevational view partly in section of the distal end and jaws of the prior art biopsy forceps instrument shown in FIG. 1 with the combination end cap of the invention.

Detailed views of the combination end cap 300 of the invention are seen in FIGS. 3 and 4. The combination end cap 300 has a cup portion 302, an integral attachment clip 314, and an integral suction cup 310 having a suction surface 310a. The cup portion 302 of the cap 300 has an open proximal end 304, a closed substantially hemispherical distal end 306, and cup walls 308. The cup portion 302 is hollow and dimensioned for receiving and holding a jaw assembly 14 as described in FIGS. 1 and 2. Preferably, the cup 302 has an inner diameter substantially equal to the outer diameter of the jaw assembly 14, thereby achieving an interference fit which holds the cap on, and the length of the cap is preferably one to one and a half times the length of the jaw assembly. The inside 304a of the proximal end 304 of the cup 302 may contain, if desired, a circumferential protrusion or lip 322 which extends partially or completely around the inside 304a of the cap for a better fastening of the cap 300 to the jaws 18 of the biopsy forceps 10.

Figure 5:
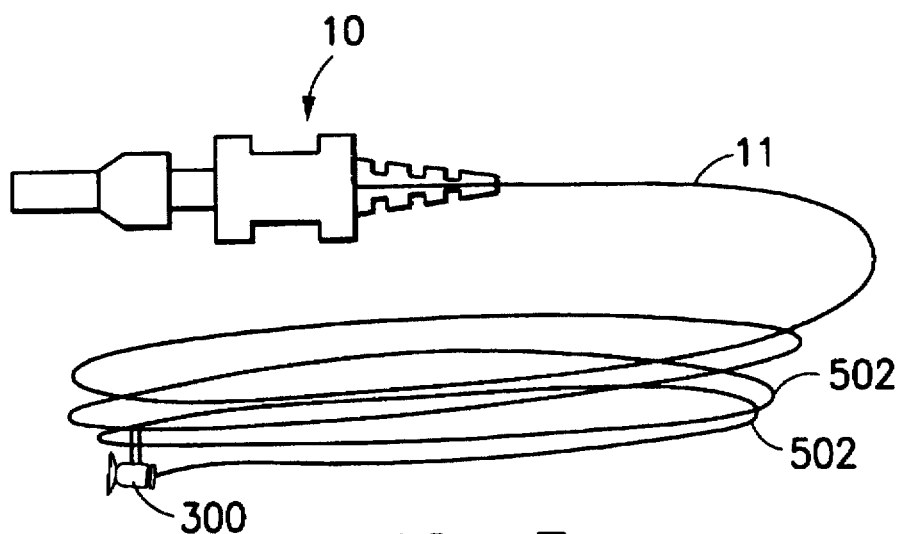
FIG. 5 is a perspective view of the combination end cap of the invention covering the jaws of the prior art biopsy forceps instrument when the coil of the forceps is wound for storing or packaging.
Figure 6:
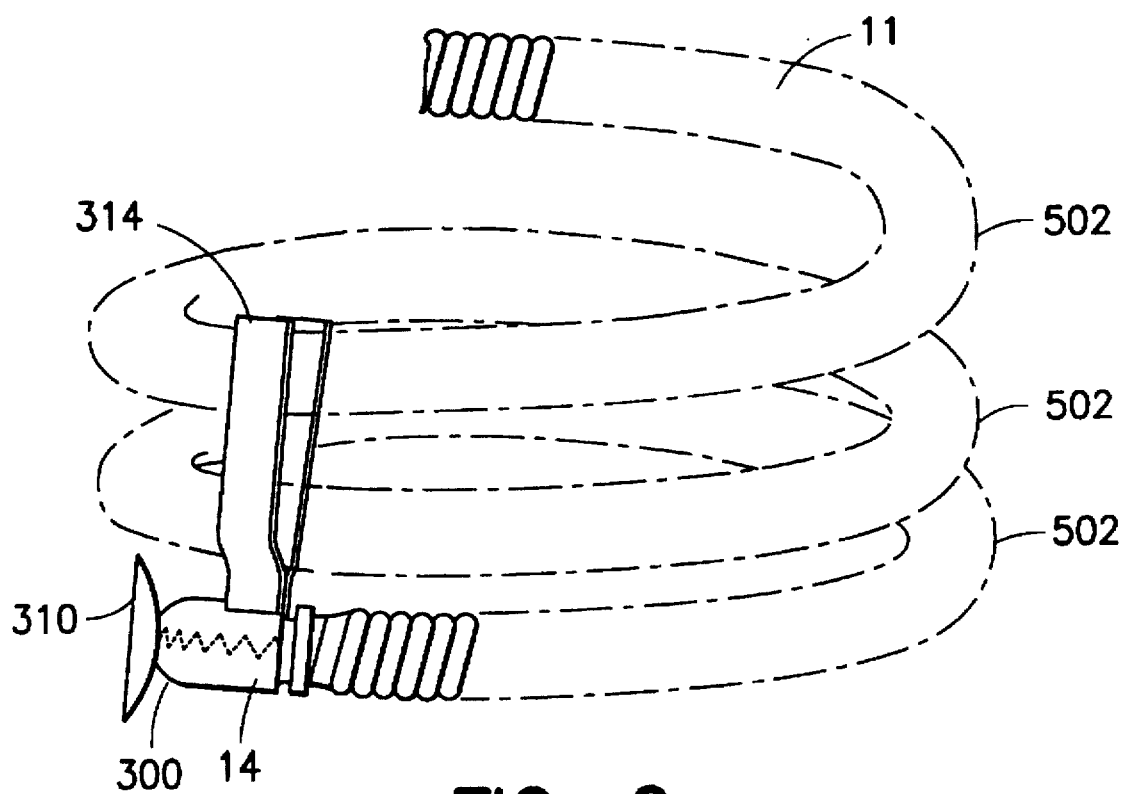
FIG. 6 is a detailed perspective view of the combination end cap of the invention and the wound coil section of the prior art biopsy forceps as shown in FIG. 5.

The attachment clip 314 of the combination end cap 300 includes two substantially parallel resilient arms 314a, 314b having mutually facing inner surfaces 315a, 315b. The inner surfaces 315a, 315b are optionally ribbed for improved grasping capability. The resilient arms 314a extend from the walls 308 of the cup 302, and are dimensioned for fitting around one or more sections of the flexible coil 11 of the biopsy forceps 10 as shown in FIGS. 5 and 6. In particular, the arms 314a and 314b each have a length preferably equal to at least twice the diameter of the flexible coil, and a width preferably equal to about one half the length of the cup portion 302. The distance separating the ribbed surfaces 315a and 315b of the resilient arms 314a and 314b is slightly smaller than that of the diameter of the flexible coil 11. It will be appreciated that when the coil 11 of the biopsy forceps is wound for packaging and the jaw assembly 14 is covered with the cup portion 302 of the end cap 300, the clip 314 can be attached to multiple sections of the flexible coil 11 to prevent the coil 11 from unwinding. After removal from the jaws, the clip 314 may also be used to affix the cap 300 to the proximal section 11a of the coil 11 (see FIG. 1) where it can then easily be retrieved for subsequent use. Also, during transport of the biopsy forceps instrument to or from cleaning (autoclaving), or for disposal, the clip 314 will hold the forceps instrument in a compact bundle for easier handling.

The integral affixing suction cup 310 is located at the closed distal end 306 of the cup portion 302 such that the suction surface 310a faces away from the cup 302. The suction cup 310 is dimensioned so as to be easily affixed to any smooth surface yet not interfere with the packaging of the biopsy forceps instrument 10. In particular, the diameter of the suction cup 310 is approximately three times that of the cup portion 302. It will be appreciated that the suction cup 310 may be used to affix the end cap 300 to any smooth surface, thus preventing inadvertent misplacement and loss of the cap. In addition, it will be appreciated that when the suction cap is used to attach to the end cap to a surface, the cap is positioned with its open end toward the practitioner. This permits the practitioner to recap the distal assembly of the biopsy forceps instrument with the use of a single hand.

The combination end cap 300 with integral clip 314 and integral suction cup 310 is preferably manufactured by any known insert molding method out of a plastic such as polyethylene or out of any other inexpensive and resilient material.

Turning now to FIGS. 5 and 6 the combination end cap and clip 300 of the invention is shown covering the jaw assembly 14 of the biopsy forceps instrument 10 and affixing the jaw assembly 14 to the looped coil 11 in order to minimize its size for packaging. Specifically, the coil 11 of the biopsy forceps 10 is wound in a layered circular-like fashion, forming multiple adjacent coil loops 502. The combination end cap 300 is placed and fastened over the closed jaw assembly 14 in a fashion similar to that described above. The clip 314 is affixed to one or more adjacent coil loops 502, which stabilizes and secures the distal end 12 and jaw assembly 14 of the biopsy forceps 10.

There has been described and illustrated herein a combination end cap for a biopsy forceps jaw assembly. While a particular embodiment of the invention has been described, it is not intended that the invention be limited thereto, as it is intended that the invention be as broad in scope as the art will allow and that the specifications be read likewise. Thus, while a combination end cap has been described having a suction cup and a clip, it will be understood that the end cap may also be made to have only the clip. Also, while particular embodiments of the integral clip and integral suction cup have been disclosed, other embodiments may also be used. For example, while the integral clip is shown to have a ribbed interior, the clip may also have a flat interior with a fastening jaw at the end. Also while the suction cup is shown to be located at the distal end of the cap, it may also be located anywhere along the side walls without interfering with the clip. In fact, the suction cup could be replaced with a flange or a set of legs which would allow the cap to be set on a horizontal surface with the opening of the cup oriented upward for a one handed insertion of the distal end of the forceps into the cap. Further, while relative sizes of the clip, suction cup, and cup portion of the end cap relative to each other and to the jaws and coil of the biopsy forceps instrument have been provided it will be appreciated that the dimensions can vary as needed. It will therefore be appreciated by those skilled in the art that yet other modifications could be made to the provided invention without deviating from its spirit and scope as so claimed.

We claim:

1. A combination of an end cap and a biopsy forceps instrument, said biopsy forceps instrument comprising a coil section with a diameter and a jaw section with a length and an outer diameter, said end cap comprising a hollow cup having an open proximal end, a closed distal end, and side walls, and an attachment means for releasably attaching said cap to the coil of the biopsy forceps instrument, said attachment means extending substantially perpendicularly from the side walls.

2. The combination according to claim 1, wherein:

said hollow cup has an inner diameter which is substantially equal to the outer diameter of the jaw section of the biopsy forceps instrument.

3. The combination according to claim 1, wherein:

said hollow cup further has a length which is in the range of one to one and a half times the length of the jaw section of the biopsy forceps instrument.

4. The combination according to claim 1, wherein:

said hollow cup has a fastening means extending inwardly from said side walls for fastening said end cap to the jaw section of the biopsy forceps instrument.

5. The combination according to claim 1, wherein:

said attachment means is a clip having two substantially parallel arms, and said clip is positioned between said distal end and said proximal end of said hollow cup.

6. The combination according to claim 5, wherein:

said parallel arms of said clip further include ribbed inner surfaces.

7. The combination according to claim 5, wherein:

said clip has a length at least twice the length of the diameter of the coil.

8. The combination according to claim 1, further comprising:

an affixing means extending from said hollow cup for affixing said cap to a surface.

9. The combination according to claim 8, wherein:

said affixing means is a suction cup which is positioned on said distal end of said hollow cup.

10. The combination according to claim 9, wherein:

said suction cup has a diameter greater than a diameter of said hollow cup.

11. A combination of an end cap and a biopsy forceps instrument, said biopsy forceps instrument comprising a coil section and a jaw section, said end cap comprising a hollow cup having an open proximal end, a closed distal end, and side walls, said open proximal end removably fitting over the jaw section, and an affixing means for affixing said cap to a planar surface, said affixing means extending from said hollow cup.

12. The combination according to claim 11, wherein:

said hollow cup further has an inner diameter which is substantially equal to the outer diameter of the jaw section of the biopsy forceps instrument.

13. The combination according to claim 11, wherein:

said hollow cup further has a length which is in the range of one to one and a half times the length of the jaw section of the biopsy forceps instrument.

14. The combination according to claim 11, wherein:

said hollow cup has a fastening means extending inwardly from said side walls for releasably fastening said combination end cap to the jaw section of the biopsy forceps instrument.

15. The combination according to claim 11, wherein:

said affixing means is a suction cup which is positioned on said distal end of said hollow cup.

16. The combination according to claim 15, wherein:

said suction cup has a diameter approximately equal to three times a diameter of said hollow cup.

17. The combination according to claim 16, further comprising:

an attachment means extending from said hollow cup for attaching said cap to the coil.

18. The combination according to claim 17, wherein:

said attachment means is a clip having two substantially parallel arms, and said clip is positioned between said distal end and said proximal end of said hollow cup.

19. The combination according to claim 18, wherein:

said parallel arms of said clip further include ribbed inner surfaces.

20. The combination according to claim 19, wherein:

said clip has a length at least twice the length of the diameter of the coil.

\* \* \* \* \*